(12) United States Patent
Logeart

(10) Patent No.: US 6,682,349 B1
(45) Date of Patent: Jan. 27, 2004

(54) DRILL ASSEMBLY FOR PREPARING A PROSTHETIC CROWN-RECEIVING TOOTH

(76) Inventor: Dominique Logeart, 21, rue Henri Thomas, 08000 Charleville-Mezieres (FR)

( * ) Notice: Subject to any disclaimer, the term of this patent is extended or adjusted under 35 U.S.C. 154(b) by 116 days.

(21) Appl. No.: 10/030,783

(22) PCT Filed: Jul. 13, 2000

(86) PCT No.: PCT/FR00/02031

§ 371 (c)(1),
(2), (4) Date: Jan. 8, 2002

(87) PCT Pub. No.: WO01/03603

PCT Pub. Date: Jan. 18, 2001

(30) Foreign Application Priority Data

Jul. 13, 1999 (FR) .............................................. 99 09207
Oct. 18, 1999 (FR) .............................................. 99 13111

(51) Int. Cl.⁷ ................................................. A61C 3/02
(52) U.S. Cl. ........................................ 433/166; 408/226
(58) Field of Search ................................. 433/165, 166; 408/226

(56) References Cited

U.S. PATENT DOCUMENTS 2,723,455 A  *  11/1955  Oberley
2,807,264 A  *  9/1957   Tuck
2,855,673 A  *  10/1958  Gruenwald
4,830,615 A  *  5/1989   Feinman et al. ............. 433/166
5,277,583 A  *  1/1994   Chalifoux ..................... 433/220
6,186,788 B1 *  2/2001   Massad ....................... 433/165
6,565,356 B2 *  5/2003   Oyamada et al. ............ 433/166

FOREIGN PATENT DOCUMENTS

DE        500538    *  6/1930  .................. 433/166
FR      2 716 795   *  9/1995
GB        379200    *  8/1932  .................. 433/165
GB        619752    *  3/1941  .................. 433/165
SU       1438757    *  11/1988 .................. 433/166

* cited by examiner

Primary Examiner—Ralph A. Lewis
(74) Attorney, Agent, or Firm—Harrison & Egbert

(57) ABSTRACT

The invention concerns a drill assembly for preparing a prosthetic crown-receiving tooth, wherein said drills (1) are of the type comprising an active part and at least an inactive part. Each of the drills (1) comprises a distal end (12) shaped like a sphere portion having an inactive part (13) and an active part (11), one of which consists of a spherical cap in apical position with a small circle (14) having a radius much smaller than its bending radius.

8 Claims, 4 Drawing Sheets

FIG. 1a
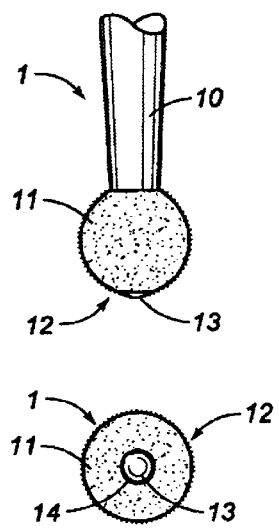
FIG. 2a
Prior Art
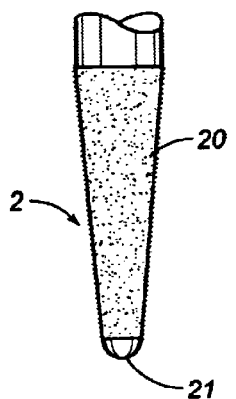
FIG. 2b
Prior Art
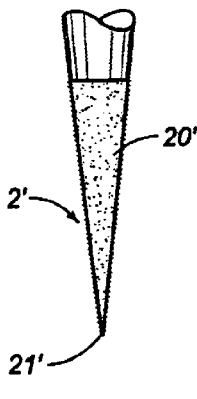
FIG. 3a
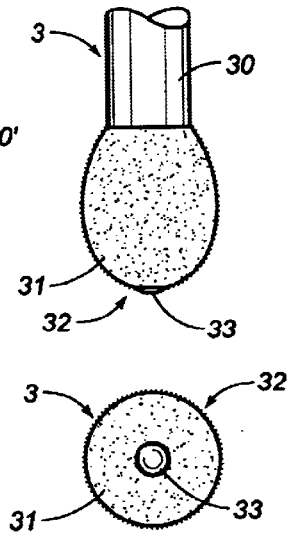
FIG. 1b
FIG. 3b
FIG. 4a
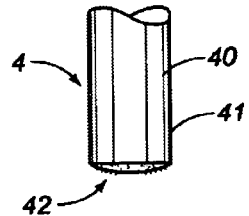
FIG. 5a
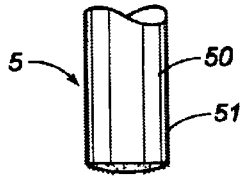
FIG. 6a
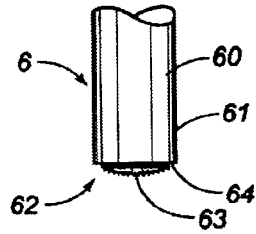
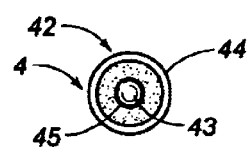
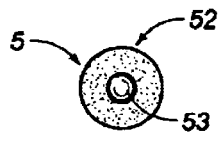
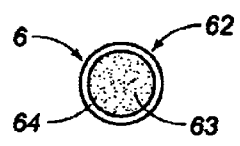
FIG. 4b
FIG. 5b
FIG. 6b

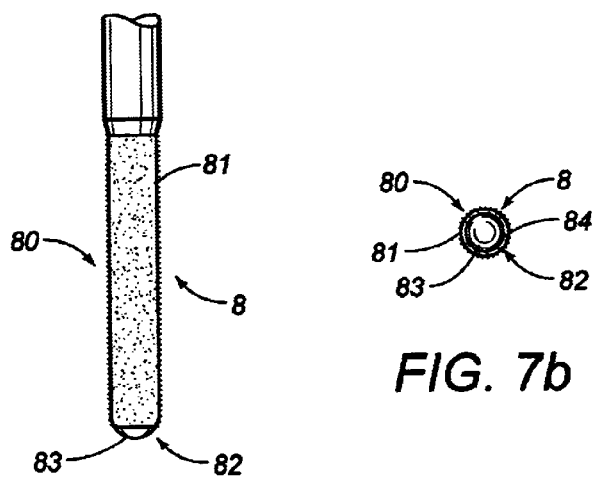
FIG. 7a
FIG. 7b
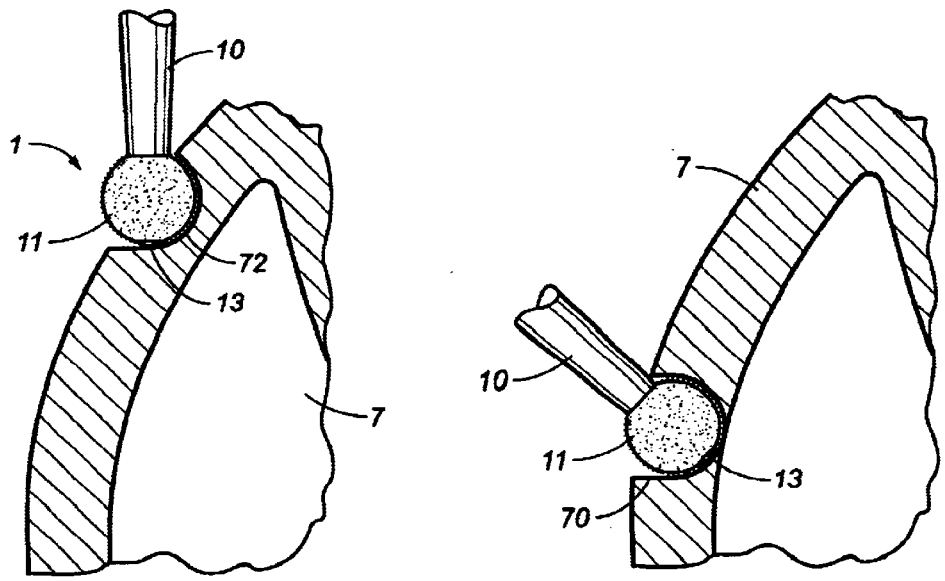
FIG. 8a
FIG. 8b

DRILL ASSEMBLY FOR PREPARING A PROSTHETIC CROWN-RECEIVING TOOTH

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The object of the present invention is a set of burs for preparing a tooth with a view to placing a prosthetic crown.

BACKGROUND OF THE INVENTION

Before placing a prosthetic crown on a tooth, it is necessary to machine said tooth, so as to remove the material that will be replaced by said prosthetic crown.

Since the size characteristics of the prosthetic crown should preferably be identical to those of the initial tooth, the four faces and the crown portion of said tooth are machined.

The operation is particularly delicate, since it is absolutely necessary to spare the papilla and the gum and to avoid damaging the adjacent teeth that are often very close to the tooth to be treated, whereby one should know that the practitioner has not always a bearing point at his disposal.

Furthermore, in order to achieve a perfect adjustment of the prosthetic crown, it is necessary for the faces to be homothetically machined according to the drawings, whereby one should know that, in the case of an incisor, the vestibular face is convex and the lingual face is concave, that, in the case of the pre-molar and the molar teeth, the faces are convex and that, in addition, the convex faces are so both in the cervical-occiusal direction and in the mesio-distal direction.

Currently, to achieve this aim, the preparation of a tooth starts by making a mesio-distal groove, then the occlusal portion and then the cervical portion are machined using the bottom of said groove as a depth control; while the last operation consists of creating a shoulder at the level of the collar, the fillet of which is preferably at a right angle in front of the gum papilla.

The drills that allow carrying out these operations are e.g. of the kind of those disclosed in FR 2,481,105 and in DE 2,012,268. These drills include, in a known way, one or several active portions and one or several inactive portions that provide the practitioner with a bearing point, without damaging the bearing area.

However, the burs of this kind do not allow the practitioner to prepare a tooth in a fully calm way, because of the requirements to be fulfilled.

Though the active portions of these burs indeed provide for a bearing point for carrying out the machining, they do not allow controlling the machining depth, namely when making the cervical fillet.

From GB 379,200 are known so-called "BATT" drills for intra-coronary use that allow, in particular, the ablation of the pulp ceiling, im order to treat the pulp eviction in the best possible way. These burs can have an ovoid or elongated shape and include, each, two portions, an active proximal portion and an inactive distal end. The bur is cylindrical, cylindrical-conical or ovoid and its distal end is semi-spherical in the case of the cylindrical and cylindrical-conical burs and parabolic in the case of the ovoid burs, the inactive portion covering at least the semi-spherical area in the case of the cylindrical and cylindrical-conical burs and a parabolic area of a height substantially equal to or larger than the radius of curvature of the end portion im the case of the ovoid burs.

Because of these features, namely the inactivity of the distal portion, these burs only allow boring out a cavity through a pivotal motion and a sliding about a point of the inactive portion. Because of its relatively large surface, namely with respect to its radius of curvature, the inactive portion is suitable only for machining a pulp ceiling and can in no way allow machining the coronary portion of a tooth.

From FR 2,716,795, there are also known dental burs including at least an inactive portion and an active portion, which are aimed at preparing a tooth with a view to placing a prosthetic crown. These drills, which must allow machining the tooth simultaneously over its full height, do not allow an accurate work and, in particular, do not to control the machining depth, namely when these drills have a flat active distal end.

BRIEF SUMMARY OF THE INVENTION

The present invention is aimed at providing a set of burs for preparing a tooth, with a view to placing a prosthetic crown, that allows coping with the various above-mentioned drawbacks.

The set of burs for preparing a tooth with a view to placing a prosthetic crown, in which said burs are of the kind including an active portion and at least one inactive portion, is characterized mainly in that each of them includes a distal end having the shape of a portion of a sphere that has an inactive portion and an active portion, one of which consists of a spherical cap in an apical position having a small circle with a radius much smaller than its radius of curvature.

According to the invention, the apical spherical cap is inactive.

According to a particular embodiment of the set of burs according to the invention, one bur includes a head having the shape of a sphere or the like.

According to another particular embodiment of the set of burs according to the invention, one bur has the shape of a cylinder, the cylindrical surface of which is inactive and the distal end of which has the shape of a spherical cap with a radius of curvature larger than that of said cylinder.

According to a particular embodiment of the set of burs according to the invention, one bur has the shape of a cylinder, its cylindrical surface being inactive, while its distal end, which has the shape of a spherical cap with a radius of curvature larger than that of said cylinder, has, besides an inactive apical cap, an inactive peripheral area, so that the active portion of said distal end extends over a spherical ring.

According to another particular embodiment of the set of burs according to the invention, one bur has a cylindrical or cylindrical-conical shape the cylindrical or cylindrical-conical surface of which is active, while the distal end is semi-spherical.

According to the invention, the apical spherical cap is active.

According to a particular embodiment of the set of burs according to the invention, one said bur has the shape of a cylinder, its cylindrical surface being inactive, while its distal end, which has the shape of a spherical cap with a radius of curvature larger than that of said cylinder, has an active apical spherical cap bordered by an inactive spherical ring.

According to another particular embodiment of the set of burs according to the invention, one said bur has the shape of a cylinder, its cylindrical surface being inactive, while its distal end, which has the shape of a spherical cap with a radius of curvature larger than that of said cylinder, has an active apical spherical cap bordered by an inactive beveled rim.

The advantages and the features of the set of burs according to the invention will become apparent when reading the following description, which refers to the attached drawing that shows one non-restrictive embodiment of it.

BRIEF DESCRIPTION OF THE SEVERAL VIEWS OF THE DRAWINGS

In the attached drawings, the following views are shown.

FIG. 1a is a partial elevation view of one bur of the set of burs according to the invention.

FIG. 1b shows a plan view of the end of the same bur.

FIGS. 2a and 2b show partial elevation views of burs of a known kind that can be used together with the set of burs according to the invention.

FIG. 3a shows a partial elevation view of another bur of the set of burs according to the invention.

FIG. 3b shows a plan view of the end of the same bur.

FIG. 4a shows a partial elevation view of another bur of the set of burs according to the invention.

FIG. 4b shows a plan view of the end of the same bur.

FIG. 5a shows a partial elevation view of another bur of the set of burs according to the invention.

FIG. 5b shows a plan view of the end of the same bur.

FIG. 6a shows a partial elevation view of another bur of the set of burs according to the invention.

FIG. 6b shows a plan view of the end of the same bur.

FIG. 7a shows a partial elevation view of another bur of the set of burs according to the invention.

FIG. 7b shows a plan view of the end of the same bur.

FIGS. 8a and 8b show schematic cross-sectional vestibular-lingual views of an incisor during the machining of the latter by means of a bur of the set of burs according to the invention.

DETAILED DESCRIPTION OF THE INVENTION

Figure 9A:
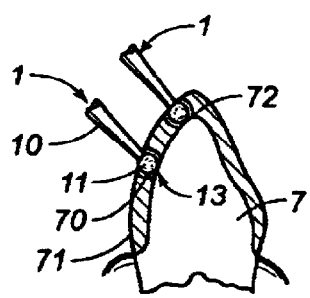
FIGS. 9a, 9b, 9c, 9d, 9e, 9f, 9g, 9h and 9I show cross-sectional vestibular-lingual views of an incisor during successive steps of its preparation by means of the set of burs according to the invention.

When referring to FIG. 1a, one can see a bur 1 that is part of the set of burs according to the invention for preparing a tooth, with a view to placing a prosthetic crown.

The bur has a smooth shaft 10 that bears, at its end, a sphere 11, the surface of which is active, except for the apical end of the distal portion 12 that consists of a non-active spherical cap 13, as shown in FIG. 1b.

The spherical cap 13 is delimited by a small circle 14 with a radius by far smaller than the radius of curvature of said spherical cap, in this case that of sphere 11. By way of an example, in the case of bur 1, the radius of the small circle 14 represents one third of the radius of curvature of sphere 11.

The distal end 12 thus includes not only an inactive apical portion, but also an active portion that is in the form of a spherical ring.

Referring to FIGS. 2a and 2b, one can see burs 2 and 2' of a known kind frequently used for preparing a tooth; bur 2 is namely a so-called "BATT" bur. Bur 2 shown in FIG. 2a has an active conical surface 20 and an inactive rounded semi-spherical end 21, while bur 2', shown in FIG. 2b, has an active conical surface 20' and an inactive sharp end 21'; burs 2 and 2' can be used in association with the set of burs according to the invention, as will be seen further in the description.

Referring to FIG. 3a, one can see a bur 3, which includes a smooth shaft 30 bearing, at its end, an out of round ball 31, the surface of which is active, as well as its semi-spherical distal end 32, except for its apical end that consists of a non-active small spherical cap 33, as shown in FIG. 3b.

When referring to FIG. 4a, one can see a bur 4 that consists of a cylinder 40, the cylindrical surface 41 of which is inactive and the distal end 42 of which has the shape of a portion of a sphere with a radius of curvature by far larger than that of cylinder 40, so that it consists of a spherical cap. There is an apical end 43 in the form of an inactive spherical cap and an inactive peripheral area 44, which border an active semi-spherical area 45, as can be seen in FIG. 4b.

When referring to FIG. 5a, one can see a bur 5 that consists of a cylinder 50, the cylindrical surface 51 of which is inactive and the distal end 52 of which, having the shape of a portion of a sphere with a radius of curvature larger than that of the cylinder 50, so that it consists of a spherical cap, is active, except for the apical end 53 that consists of an inactive spherical cap, as can be seen in FIG. 5b.

When referring now to FIGS. 6a and 6b, one can see a bur 6 that consists of a cylinder 60, the cylindrical surface 61 of which is inactive and the distal end 62 of which, having the shape of a portion of a sphere with a radius of curvature by far larger than that of the cylinder 60, so that it consists of a spherical cap, has an active apical portion 63 having the shape of a spherical cap peripherally bordered by an inactive area 64 having the shape of a spherical ring.

One should note that, according to a variant, not shown, the inactive area 64 can be formed by a beveled rim.

When referring now to FIG. 7, one can see a bur 8 that consists of a cylinder 80 having an active cylindrical surface 81, as well as a distal end 82 having an active semi-spherical shape, except for the apical portion 83 that is inactive and that has the shape of a cap the small circle 84 of which is by far smaller than that of the semi-spherical distal portion 82.

According to a variant, not shown, of the bur 8, the cylinder 80 can be replaced by a cylindrical-conical body.

When referring now to FIGS. 8a and 8b, one can see the way of use of a bur from the set of burs according to the invention, in this case a spherically shaped bur 1, on an incisor 7, the striped area of the latter corresponding to the material thickness to be removed.

In FIG. 8a, it can be seen that bur 1 is laterally brought close to the incisor 7 and parallel to the axis of the latter. The penetration of sphere 11 into the material is not possible axially, because of the inactive cap 13; it is limited in depth by the smooth shaft 10 that abuts against the upper edge of the created cavity.

When referring now to FIG. 8b, one can see that, by inclining the bur 1 with respect to the incisor 7, the depth of the created cavity can be increased, which depth is then limited by the cap 13. From the position shown, the sphere 11 can be moved only according to a mesio-distal motion, while maintaining a constant depth, without any risk of perforation. The choice of the diameter of the sphere 11 determines the depth of the cavity or of the groove to be made.

Hereafter will be described the way of use of the burs 1, 2, 2', 3, 4, 5, 6 and 8, with reference to FIGS. 9a, 9b, 9c, 9d, 9e, 9f, 9g, 9h and 9i and to FIGS. 10a, 10b, 10c, 10d, 10e, 10f and 10g, which represent different steps of the preparation of an incisor 7.

Figure 10A:
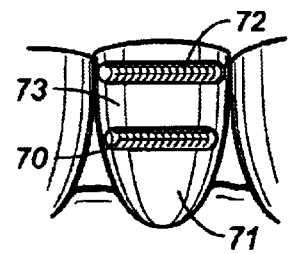
FIGS. 10a, 10b, 10c, 10d, 10e, 10f and 10g show front schematic views of the same incisor during some of the same successive steps of the same preparation.

When referring to FIGS. 9a and 10a, one can see that the first step of the preparation consists in creating in the first place, at half height of the vestibular convex face 71, by means of a bur 1, a mesio-distal groove 70, as shown only in FIG. 1a, of a desired thickness, while sparing the adjacent teeth, i.e. choosing a bur 1 of an adequate diameter. As we have seen above, the groove 70 is created while resting on the shaft 10 and inclining it in order to achieve a sufficient penetration, which is possible on the vestibular face 71.

Bur 1 can work only according to a swinging motion in locked positions on the shaft and on the inactive end 13, which limits the penetration of the bur 1.

The next step consists in creating in the vestibular face 71 a mesio-distal groove 72 at the occlusal level in the vicinity of the incisive edge, about 2 millimeters away from it, also by means of bur 1 used in the same way as for creating the groove 70.

The next step, not shown, consists in marking the bottom of the groove 72 by applying on it a dyestuff, the bottom of the groove 72 serving as a depth reference.

Figure 9B:
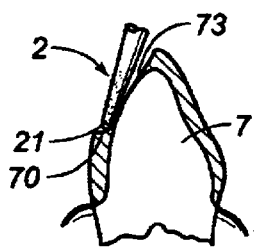
Figure 10B:
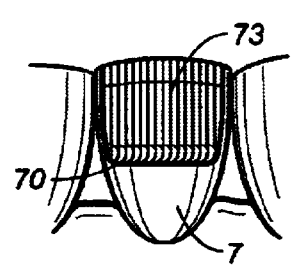

When referring now to FIGS. 9b and 10b, one can see that the next step consists in removing as homothetically as possible the vestibular-occlusal face 73 by means of a bur 2, while resting, with the inactive end 21 of the latter, in the groove 70 and taking care not to remove the marking on the bottom of the groove 72.

After machining the vestibular-occlusal face 73, it should preferably be marked completely, in order to preserve it during the next steps.

Figure 9C:
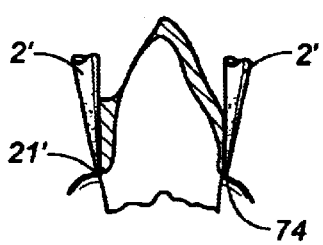
Figure 10C:
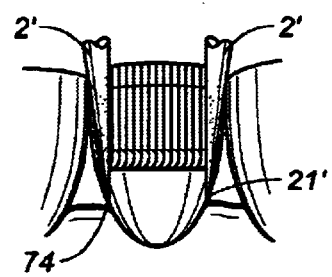

When referring now to FIGS. 9c and 10c, one can see that the next step consists in re-tapering the tooth 7 through machining all the faces of the tooth, in the direction of the axis of insertion, by means of a bur 2', or 2, while resting at the cervical level 74 with the inactive end 21' or 21, while sparing the papilla and the adjacent teeth.

The choice of the bur depends on the space between teeth when the teeth do not enter into contact with each other, a bur 2 is preferably used.

The next steps consist in making the cervical fillet, which is the most delicate operation during the preparation of the tooth 7.

Figure 9D:
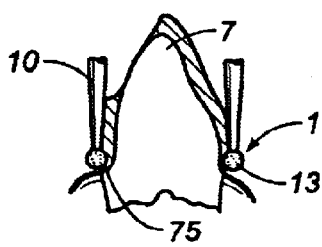
Figure 10D:
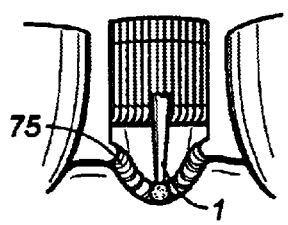
Figure 10E:
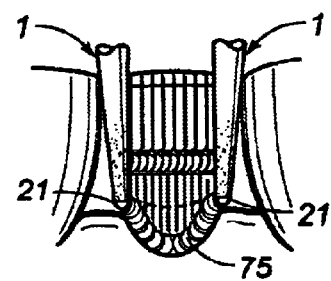

When referring to FIGS. 9d and 10d, one can see that in a first moment is created, within the desired limit, a peripheral pre-cervical groove 75, by means of a bur 1 the active spherical end 11 of which has a sufficiently small diameter to be able to pass through the space between teeth without damaging the adjacent teeth.

As can be seen in FIGS. 9a and 10a, the groove 75 of the bed of portion 21 of bur 2 that tapers everything.

One should note that this operation can also be carried out by means of bur 8 or any of its variants.

Figure 9E:
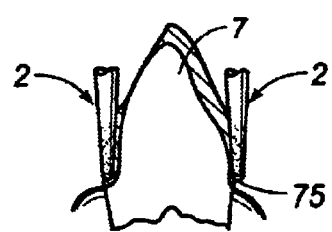
Figure 9F:
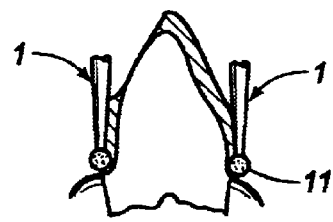
Figure 10F:
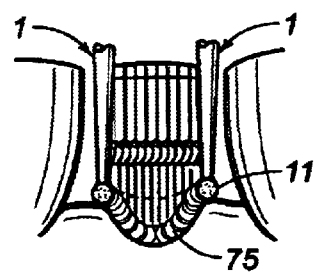

Afterwards, as shown in FIGS. 9f and 10f, one has to use again a bur 1 of an appropriate diameter, which can be blocked by its shaft 10 and its inactive cap 13, and swung according to an axis close to the axis of insertion, in order to maintain over the full periphery a groove of a constant thickness.

Figure 9G:
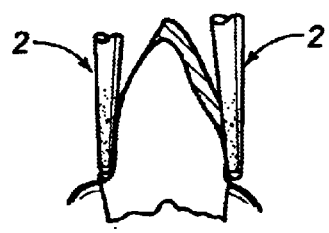
Figure 10G:
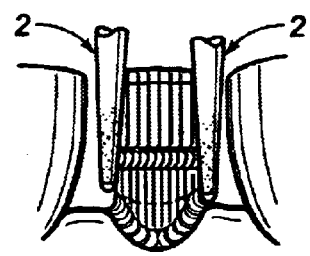

Then, with reference to FIGS. 9g and 10g, a bur 2 is used to taper the tooth 7. The burs 1 and 2 or 8 will be used alternately, until achieving a fillet 76 of about 10/10.

One should note that for carrying out the fillet, one preferably uses a bur 8, which can allow avoiding the alternate use of a bur 2 and a bur 1, since, contrarily to bur 2, the semi-spherical distal portion 82 of bur 8 is an active portion, which authorizes a machining substantially equivalent to that of bur 1.

Figure 9H:
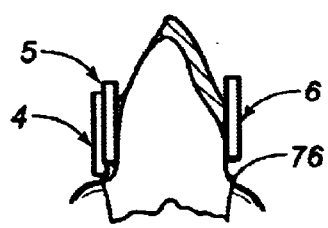
Figure 9I:
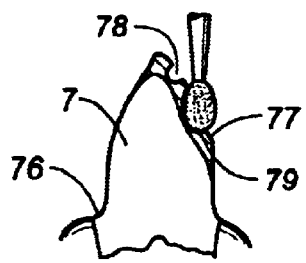

The finishing of the fillet 76 is shown in FIG. 9h; it is achieved by using successively burs 4, 5 and 6.

Bur 4 is used to regularize the surface of fillet 76 and bring it into its final situation. The inactive peripheral area 44 allows the bur 4 to be placed at the final level of the sulcus, by softly pushing back the papilla without attacking it.

On the other hand, bur 4 can round the cervical-axial angle, hence, bur 5 can cope with this drawback, however, taking care to keep it constantly in contact with the axial wall, in order to avoid creating an undercut at that level and destroying the papilla.

Regularizing the surface of the fillet can also be done by means of bur 6, the inactive peripheral area 64 of which allows, on the one hand, limiting an eventual sinking, on the other hand, avoiding creating an undercut and, furthermore, avoiding attacking the gum papilla.

The next step consists in treating the lingual face 77, which is concave, by reducing it, as well as the incisive edge, by means of a bur 3, as shown in FIG. 10i, after having created in it, in the same way as for the vestibular-occlusal face 73, two mesio-distal grooves 78 and 79 by means of a bur 1.

Finally, when the fillet has been carried out, the tooth 7 can be polished so as to eliminate the various markings used, while taking care not to touch the fillet that must remain very clearly at about 90°, in front of the gum papilla.

The burs 1, 3, 4, 5 and 8 according to the invention, used as described above, allow preparing a tooth without any risk of damaging it.

They cannot dig axially, since their apical end is inactive and arranged in the same convex plane as the active surface.

As regards bur 6, it allows, complementarily to burs 4 and 5, finishing the cervical fillet, the rounded shape of its distal end 62 facilitating controlling its displacement.

The burs object of the present invention allow machining the surface of a tooth with their distal end, while impeding or limiting its axial penetration, which authorizes a highly controlled and, thus, entirely safe work.

I claim:

1. A set of burrs for preparing a tooth for placement of a prosthetic crown, each of the set of burs comprising a burr having an abrasive portion and at least one non-abrasive portion, said burr having a distal end having a shape of a portion of a sphere, the non-abrasive portion being a spherical cap in an apical position defining a small circular perimeter having a radius that is substantially smaller than a radius of curvature of said portion of a sphere.

2. The set of burrs of claim 1, said distal end being abrasive other than said spherical cap.

3. The set of burrs of claim 1, wherein one of the set of burrs has a head of a spherical shape.

4. The set of burrs of claim 1, wherein one of the set of burrs is of a cylindrical having a cylindrical outer surface, said cylindrical outer surface being non-abrasive, said spherical cap having a radius of curvature larger than a radius of curvature of said cylindrical shape.

5. The set of burrs of claim 4, wherein said spherical cap has a non-abrasive peripheral area and an abrasive ring extending between said peripheral area and an end area at said apical position.

6. The set of burrs of claim 1, wherein one of the set of burrs has a cylindrical with an outer surface that is abrasive.

7. The set of burrs of claim 4, wherein said spherical cap of said one of the set of burrs has an end area at said apical position that is abrasive, said spherical cap having a non-abrasive ring extending around said end area.

8. The set of burrs of claim 7, wherein said non-abrasive ring is a non-abrasive beveled rim.

* * * * *